United States Patent [19]

Lucast et al.

[11] Patent Number: 5,407,717
[45] Date of Patent: Apr. 18, 1995

[54] CROSSLINKED ABSORBENT PRESSURE SENSITIVE ADHESIVE AND WOUND DRESSING

[75] Inventors: Donald H. Lucast, St. Paul; Cheryl L. Moore, Afton; Ruth A. James, Minneapolis, all of Minn.

[73] Assignee: Minnesota Mining and Manufacturing Company, St. Paul, Minn.

[21] Appl. No.: 47,637

[22] Filed: Apr. 14, 1993

[51] Int. Cl.$^6$ .................... A61F 13/02; C08F 226/10
[52] U.S. Cl. ........................................ 428/46; 526/264
[58] Field of Search ........................... 428/41; 526/264

[56] References Cited

U.S. PATENT DOCUMENTS

| Re. 24,906 | 12/1960 | Ulrich | 206/59 |
|---|---|---|---|
| Re. 33,353 | 9/1990 | Heinecke | 428/140 |
| 3,121,021 | 2/1964 | Copeland | 117/122 |
| 3,321,451 | 5/1967 | Gander | 260/79.3 |
| 3,475,363 | 10/1969 | Gander | 260/29.7 |
| 3,532,652 | 10/1970 | Zang et al. | 260/23 |
| 4,140,115 | 2/1979 | Schonfeld | 128/156 |
| 4,165,266 | 8/1979 | Stueben et al. | 204/159 |
| 4,181,752 | 1/1980 | Martens et al. | 427/54.1 |
| 4,300,820 | 11/1981 | Shah | 351/160 |
| 4,337,325 | 6/1982 | Shah | 525/205 |
| 4,370,380 | 1/1983 | Shah | 428/355 |
| 4,499,896 | 2/1985 | Heinecke | 128/156 |
| 4,737,410 | 4/1988 | Kantner | 428/343 |
| 4,737,559 | 4/1988 | Kellen et al. | 526/291 |
| 4,842,597 | 6/1989 | Brook | 604/368 |
| 4,871,812 | 10/1989 | Lucast et al. | 525/186 |
| 5,088,483 | 2/1992 | Heinecke | 602/46 |
| 5,153,040 | 10/1992 | Faasse, Jr. | 428/40 |
| 5,160,315 | 11/1992 | Heinecke et al. | 602/57 |

FOREIGN PATENT DOCUMENTS

| 51935 | 5/1982 | European Pat. Off. | A61F 13/02 |
|---|---|---|---|
| 0130080 | 1/1985 | European Pat. Off. | |
| 2115431 | 9/1983 | United Kingdom | C09J 3/14 |

OTHER PUBLICATIONS

"Radiation Curing of Pressure Sensitive Adhesives," vol. 20, No. 611984 (with translation).
"Viscoelastic Properties of Polymers," John D. Ferry, 3rd Edition, John Wiley and Sons, 1980, Chapter 1.
"Treatise on Adhesion and Adhesives," R. L. Patrick—Editor, vol. 2, Marcel Dekker Inc., 1969, Section Materials/Pressure Sensitive Adhesive.
"Properties and Structure of Polymers," Tobolsky, John Wiley and Sons, 1960, Chapter II, Section 6.
"Handbook of Pressure Sensitive Adhesive Technology," C. A. Dahlquist, Donatas Satas–Editor, Van Norstrand Reinhold Company, 1982, Chapter 5.
"Textbook of Polymer Science," Fred W. Billmeyer, Jr., pp. 84–85, Second Edition, Wiley-Interscience (1971).
Chemical Abstracts, vol. 83, No. 24, 15 Dec. 1975, Columbus, Ohio; Abstract No. 194465, "Pressures Sensitive Adhesive Compositions" p. 57; column 1.

Primary Examiner—Joseph L. Schofer
Assistant Examiner—Wu C. Cheng
Attorney, Agent, or Firm—Gary L. Griswold; Walter N. Kirn; Amy J. Hoffman

[57] ABSTRACT

Crosslinked, absorbent pressure sensitive adhesive compositions are disclosed comprising an acrylate or methacrylate ester of an alcohol, a hydrophilic alkylene oxide acrylate, a hydrophilic N-vinyl lactam, and an effective amount of a crosslinking agent. The compositions have an enhanced skin adhesion profile and are moderately absorbent. Also disclosed are precursor adhesive compositions and low-profile wound dressings.

5 Claims, No Drawings

CROSSLINKED ABSORBENT PRESSURE SENSITIVE ADHESIVE AND WOUND DRESSING

FIELD OF THE INVENTION

The invention broadly relates to pressure sensitive adhesive compositions, precursor compositions for such adhesives, and wound dressings using such adhesive compositions. More specifically, the invention relates to biologically compatible, absorbent, pressure sensitive adhesive compositions, precursor compositions for such adhesives, and wound dressings using such adhesive compositions.

BACKGROUND OF THE INVENTION

Pressure sensitive adhesives have long been used in the manufacture of medical tapes and dressings intended for attachment to the skin.

Pressure sensitive adhesives intended for use in attaching tapes and/or dressings to the skin must possess a number of physical, chemical and biological characteristics including (i) biological compatibility with skin over extended periods of continuous contact, (ii) biological compatibility with surgical incisions and lesions, and (iii) a bonding strength sufficient to prevent premature peeling of the tape/dressing from the skin but low enough to prevent skin irritation upon removal of the tape/dressing.

Acrylate-Based Pressure Sensitive Adhesives

Acrylate-based pressure sensitive adhesive tapes have been used for many years in medical and surgical applications. Acrylate-based pressure sensitive adhesive tapes are generally biologically compatible and provide acceptable adhesion to the skin. One such acrylate-based pressure sensitive adhesive tape having acceptable skin adhesion performance is disclosed in U.S. Pat. No. 3,121,021 issued to Copeland.

Acrylate-based pressure sensitive adhesive tapes are known to suffer from adhesion buildup after extended contact with the skin. Excessive adhesion buildup causes the tape to strip skin from the body upon removal from the skin to the point of producing moderate pain and prolonged skin irritation. U.S. Pat. No. 3,321,451 issued to Gander discloses that the inclusion of certain amine salts into an acrylate-based pressure sensitive adhesive facilitates the removal of pressure sensitive adhesive tape from the skin by permitting the bonding strength of the tape to be reduced by soaking the tape with water. U.S. Pat. No. 3,475,363, also issued to Gander, attempts to overcome the objectionable adhesion buildup associated with acrylate-based pressure sensitive adhesives by including the crosslinking agent dimethylaminoethyl methacrylate into the adhesive.

U.S. Pat. No. 3,532,652 issued to Zang discloses that the adhesion buildup observed with acrylate-based pressure sensitive adhesives is caused by the migration of body fluids, such as skin oils, into the adhesive. Zang discloses that partially crosslinking an acrylate-based pressure sensitive interpolymer adhesive with polyisocyanate overcomes the adhesion buildup problem.

U.S. Pat. No. 4,140,115 issued to Schonefeld discloses that the skin-stripping irritation associated with the removal of acrylate-based pressure sensitive adhesive tapes can be alleviated by blending an unreacted polyol having a fatty acid ester pendant moiety into the acrylate-based pressure sensitive adhesive. We observe that such an adhesive would tend to leave objectionable residue on the skin after removal of the tape.

Crosslinking of Pressure Sensitive Adhesives

The crosslinking of acrylate-containing polymers using a photosensitive crosslinking agent, such as a benzophenone, is taught by U.S. Pat. No. 4,181,752 issued to Martens et al.

U.S. Pat. No. 4,165,266 issued to Stueben et al. discloses a pressure sensitive adhesive composition synthesized from a poly(vinyl alkyl ether), a monoacrylate monomer and a photoinitiator, such as benzophenone.

A solvent and heat resistant pressure sensitive adhesive is disclosed in a Japanese language review article authored by Toshio Okada entitled *Radiation Curing of Pressure sensitive Adhesives*, Volume 20, No. 611984. The pressure-sensitive adhesive is a copolymer of benzoin acrylate and an acrylate monomer, such as 2-ethylhexylacrylate, cured by exposure to ultraviolet radiation. We believe that the degree of crosslinking in such a composition would result in an adhesive having unacceptably low adhesion strength for use in securing a tape or dressing to the skin.

While the varied adhesives disclosed above provide a wide range of beneficial properties, a substantial need still exists for a low-cost, absorbent, biologically compatible, pressure sensitive adhesive useful in the manufacture of a low-profile wound dressing having a moderate capacity for absorbing wound exudate.

SUMMARY OF THE INVENTION

Pressure-Sensitive Adhesive

The invention is a moderately absorbent, biologically compatible, pressure sensitive adhesive useful in the manufacture of a low-profile wound dressing with an acceptable adhesion to skin arid a moderate capacity for absorbing wound exudate without objectionable adhesion, buildup after extended contact with the skin. The adhesive may be formulated to provide a substantially transparent dressing so that the wound may be inspected and monitored without removing the dressing.

A first aspect of the invention is an absorbent, biologically compatible, pressure sensitive adhesive comprising a crosslinked copolymer of (a) an acrylate monomer selected from the group consisting of (i) an acrylate or methacrylate ester of a non-tertiary $C_{4-12}$ alcohol, and (ii) an acrylate or methacrylate ester of a mixture of non-tertiary $C_{1-14}$ alcohols with a resultant average of between about 4–12 carbon atoms per alcohol molecule; (b) a hydrophilic alkylene oxide acrylate monomer having an average of about 3 to 40 alkylene oxide units; (c) a hydrophilic N-vinyl lactam monomer; and (d) a crosslinking agent effective for crosslinking the copolymer.

The pressure sensitive adhesive can be chemically tailored, within physically defined parameters, to produce a skin compatible adhesive having a unique combination of properties. The properties of the novel pressure sensitive adhesive include (i) biological compatibility with human skin over extended periods of continuous contact, (ii) biological compatibility with surgical incisions and lesions, (iii) a bonding strength sufficient to preventing premature peeling of the tape/dressing from the skin but low enough to prevent skin irritation upon removal of the tape/dressing, (iv) a moderate absorbency sufficient to permit use of an otherwise low-absorbent tape/dressing over a surgical incision or lesion producing a moderate amount of fluid exudate, (v) a conformability sufficient to permit a tape/dressing to follow to the contours of the body, and (vi) a cohesive strength effective for maintaining the adhesive in position between the skin and the backing of the tape/dressing during application and use.

Precursor Composition for Manufacture of a Pressure-Sensitive Adhesive

A second aspect of the invention is a precursor composition useful for making an absorbent, biologically compatible, pressure sensitive adhesive. The precursor composition comprises an uncrosslinked copolymer of (a) an acrylate monomer selected from the group consisting of (i) an acrylate or methacrylate ester of a non-tertiary $C_{4-12}$ alcohol, and (ii) an acrylate or methacrylate ester of a mixture of non-tertiary $C_{1-14}$ alcohols with a resultant average of between about 4–12 carbon atoms per alcohol molecule; (b) a hydrophilic alkylene oxide acrylate monomer having an average of about 3 to 40 alkylene oxide units; (c) a hydrophilic N-vinyl lactam monomer; and (d) a crosslinking agent effective for crosslinking the copolymer.

Wound Dressing

A third aspect of the invention is a wound dressing comprising (i) a substrate (ii) an absorbent pressure sensitive adhesive coated upon a major surface of the substrate, and (iii) a release liner protectively sandwiching the adhesive between the substrate and the liner. The pressure sensitive adhesive comprising a crosslinked copolymer of (a) an acrylate monomer selected from the group consisting of (i) an acrylate or methacrylate ester of a non-tertiary $C_{4-12}$ alcohol, and (ii) an acrylate or methacrylate ester of a mixture of non-tertiary $C_{1-14}$ alcohols with a resultant average of between about 4–12 carbon atoms per alcohol molecule; (b) a hydrophilic alkylene oxide acrylate monomer having an average of about 3 to 40 alkylene oxide units; (c) a hydrophilic N-vinyl lactam; and (d) a crosslinking agent effective for crosslinking the copolymer.

Copolymerizing of a crosslinking agent into the backbone of the pressure sensitive adhesive copolymer greatly increases crosslinking efficiency and permits the copolymer to be crosslinked after formation of the copolymer. The increased crosslinking efficiency permits very minor amounts of crosslinking agent to achieve useful degrees of crosslinking.

Use of the preferred photosensitive crosslinking agent in the copolymer of this invention allows the use of solventless coating techniques because the copolymer need not be crosslinked until after it is coated upon a support member.

These and various other advantages and features of novelty which characterize the invention are pointed out with particularity in the claims annexed hereto and forming a part hereof. However, for a better understanding of the invention, its advantages, and objects obtained by its use, reference should be had to the accompanying descriptive matter, in which there is illustrated and described preferred embodiments of the invention.

Detailed Description of Embodiments of the Invention

The first aspect of the invention is a biologically compatible, moderately absorbent, pressure sensitive adhesive composition which is a crosslinked copolymer of (a) a hydrophobic acrylate monomer (monomer A), (b) a hydrophilic alkylene oxide acrylate monomer (monomer B), (c) a hydrophilic N-vinyl lactam (monomer C), and (d) a mono-ethylenically unsaturated crosslinking agent (monomer PX). The PX monomer is preferably a photosensitive crosslinking agent effective for crosslinking the copolymer upon exposure to ultraviolet radiation.

A second aspect of the invention is a precursor composition useful for manufacturing the pressure sensitive adhesive composition described above. The precursor composition comprises the copolymer of A, B, C and PX described above prior to crosslinking of the copolymer.

A third aspect of the invention is a wound dressing for use over surgical incisions or lesions exuding a moderate amount of fluids. The dressing comprises a substrate coated on a major surface with the absorbent pressure sensitive adhesive composition described above, and a release liner protectively sandwiching the adhesive between the substrate and the liner.

The properties and characteristics of the adhesive compositions of this invention are based upon a synergistic interaction of the various individual components. Consequently, efforts to describe the attributes contributed and/or influenced by each of the individual components is not necessarily indicative of the attributes possessed by the final adhesive composition. Such descriptions should therefore be used only as an indication of general trends and as a guide to those attributes which should be carefully considered when selecting the other components of the composition. For example, monomer B impacts absorbency such that incorporation of a minor proportion of monomer B in the adhesive would tend to produce an adhesive having reduced absorbency. However, the overall absorbency of the adhesive may be returned to an acceptable level by selecting a highly absorbent monomer C, increasing the amount of monomer C in the adhesive, etc.

The Monomers

Monomer A

Monomer A is a hydrophobic acrylate monomer which contributes to the visco-elastic properties of the copolymer. The monomer is selected from the group consisting of (i) an acrylate or methacrylate ester of a non-tertiary $C_{4-12}$ alcohol, and (ii) an acrylate or methacrylate ester of a mixture of non-tertiary $C_{1-14}$ alcohols with an average of between about 4–12 carbon atoms per alcohol molecule. Useful acrylate and methacrylate alcohol esters include specifically, but not exclusively, the acrylic acid and methacrylic acid esters of 1-butanol, 1-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, and 1-dodecanol. Mixtures of these alcohols are available from Exxon under the Exxal family mark. A preferred alcohol mixture for use in synthesizing monomer A is Exxal-8.

The copolymer includes about 30 to 70 wt %, preferably about 40 to 50 wt % monomer A based upon the total weight of all monomers in the copolymer. Inclusion of less than about 30 wt % monomer A tends to produce an adhesive which is excessively hydrophilic to the point of losing cohesive strength when exposed to more than modest amounts of fluid. Inclusion of greater than about 70 wt % monomer A tends to produce an adhesive with insufficient absorbency.

Monomer B

Monomer B is a hydrophilic alkylene oxide acrylate. The synthesis of monomer B employs commercially available starting materials and widely known and accepted conventional techniques. For example, monomer B may be prepared by reacting an $\alpha,\beta$-unsaturated carboxylic acid, such as acrylic acid or methacrylic acid, with an equimolar amount of a monoalcohol of a poly(lower alkylene oxide). The esterification reaction is generally conducted under anhydrous conditions in an organic solvent, such as toluene, which preferably forms an azeotropic mixture with the water which is generated by the esterification reaction. Typically, the alcohol is combined with the organic solvent and the unsaturated carboxylic acid is then added.

The reaction is conducted in the presence of an acid catalyst, such as para-toluenesulfonic acid, and a free-radical inhibitor, such as copper powder. The reaction mixture is refluxed for several hours under a nitrogen atmosphere and the resultant water removed by azeotropic distillation.

Suitable polyalkylene oxides which may be used to prepare the preferred B monomers using the above-described procedure include Carbowax TM 350, Carbowax TM 550, Carbowax TM 750, Carbowax TM 2000 and Carbowax TM 5000 (i.e., the methoxypoly(ethylene oxide) ethanols of about 350 MW, 550 MW, 750 MW, 2000 MW and 5000 MW, respectively, which are commercially available from Union Carbide Corp. The polyalkylene oxide of choice is polyethylene oxide having an average of from 3 to 40 polyethylene (EO) units, preferably 5 to 20 EO units, per molecule.

The copolymer includes about 15 to 40 wt %, preferably about 20 to 30 wt % monomer B based upon the total weight of all monomers in the copolymer. Inclusion of less than about 15 wt % monomer tends to produce an adhesive having reduced absorbency and reduced transparency. Inclusion of greater than about 40 wt % monomer B tends to produce an adhesive having reduced tack.

Monomer C

Monomer C is a hydrophilic N-vinyl lactam which is copolymerizable with monomers A, B and PX. The monomer reinforces the adhesive and contributes modest absorbency and improved cohesiveness to the adhesive composition.

Monomer C is an N-vinyl lactam. Preferred N-vinyl lactams are N-vinylpyrrolidone and N-vinyl-2-caprolactam.

The copolymer includes about 15 to 50 wt %, preferably about 20 to 30 wt % monomer C based upon the total weight of all monomers in the copolymer. Inclusion of less than about 15 wt % monomer C tends to produce an adhesive having a reduced cohesiveness observed as an unsatisfactory "skin adhesion profile". Inclusion of greater than about 50 wt % monomer C tends to produce an adhesive with reduced tack and reduced conformability.

Crosslinking Monomer PX

Crosslinking monomer PX is a copolymerizable, monoethylenically unsaturated crosslinkable monomer. The ethylenically unsaturated group is copolymerizable with the A, B and C monomers to form the backbone of the polymer chain. The PX monomer is preferably one which may be crosslinked after coating of the adhesive composition upon a support such as by exposure to ultraviolet radiation.

A preferred PX monomer is a monoethylenically unsaturated aromatic ketone. Such PX monomers are known to absorb ultraviolet radiation and form a triplet excited state through intersystem crossing. The excited-state molecules abstract hydrogen radicals from the polymer chain leaving free radical sites which combine to form crosslinks. The semi-pinacol radical on the aromatic ketone can also produce crosslinking.

A hydroxyl group positioned ortho to the carbonyl group on the aromatic ring is known to inhibit the ability of aromatic ketones to effect crosslinking. Accordingly, the aromatic ketone monomer must be free of ortho-aromatic hydroxyl groups to be effective as a photosensitive crosslinking agent.

Suitable PX monomers are represented by the general formula:

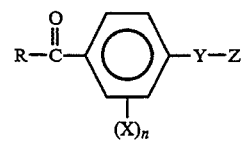

wherein:

R: is a lower alkyl or phenyl which may be substituted with one or more halogen atoms, alkoxy groups or hydroxyl groups except that when R is a hydroxy substituted phenyl the hydroxyl group(s) must be positioned meta or para to the aromatic carbonyl;

X: is halogen, alkoxy or hydroxyl provided that when X is a hydroxyl group it is positioned meta or para to the aromatic carbonyl;

Y: is a divalent linking group which is preferably a covalent bond, an oxygen atom(—O—), an amino group (—NR$^1$— wherein R$^1$ is hydrogen or lower alkyl), an oxyalkyleneoxy group (—O—R$^2$—O— wherein R$^2$ is an alkylene group), a carbamoylalkyleneoxy group (—O—R$^2$—O—(O)—N—(R-$^1$)—R$^3$— wherein R$^3$ is a covalent bond or an alkyleneoxy group such as —R$^2$—O—);

Z: is alkenyl or ethylenically unsaturated acyl group; and n: is an integer from 0 to 4.

Particularly preferred PX monomers are the acryloxybenzophenones such as 4-acryloxybenzophenone.

The copolymer includes about 0.01 to 2 wt %, preferably about 0.025 to about 0.5 wt % PX monomer based upon the total weight of all monomers in the copolymer. A PX content of less than about 0.025 wt % tends to produce an adhesive with reduced cohesive strength while a PX content of greater than about 2 wt % tends to produce an adhesive with reduced tack.

It will be understood that other forms of radiation can be used to cross-link the pressure sensitive adhesive of the present invention. For example, electron beam radiation can be used to cross-link the adhesives of the present invention. In such an instance, the PX monomer would become an optional component in the pressure sensitive adhesive composition.

Properties and Characteristics

Inherent Viscosity

Inherent viscosity (IV) is recognized as a relative measure of polymer molecular weight. In order to achieve the desired creep compliance and skin adhesion profile the inherent viscosity of the uncrosslinked copolymer of this invention should be between about 0.5 to 1.4 dl/g when measured in tetrahydrofuran (THF). More preferably, the inherent viscosity is between about 0.5 to 1.1 dl/g, most preferably between about 0.6 to 0.95 dl/g when measured in THF.

Creep Compliance

The fundamentals of creep compliance ($J_3$) as they relate to polymeric materials and, in particular, to viscoelastic polymers is covered in "*Viscoelastic Properties of Polymers*", John D. Ferry, 3rd Edition, John Wiley and Sons, 1980, Chapter 1; "*Treatise on Adhesion and Adhesives*", R. L. Patrick—Editor, Volume 2, Marcel Dekker Inc., 1969, Section entitled "Materials"/"Pressure Sensitive Adhesives"; *Properties and Structure of Polymers*, Tobolsky, John Wiley and Sons, 1960, Chapter II, Section 6; and "Handbook of Pressure Sensitive Adhesive Technology", C. A. Dahlquist, Donatas Satas—Editor, Van Norstrand Reinhold Company, 1982, Chapter 5.

The creep compliance of the adhesive composition of this invention is dependent upon several factors including the specific type and relative amounts of monomers A, B, C and PX in the copolymer and the degree to which the copolymer is polymerized. Generally, an increase in the amount of PX monomer will result in an increase in the degree of crosslinking within the copolymer and thereby decrease the creep compliance of the copolymer. Similarly, an increase in the degree to which the copolymer is polymerized will increase the length of the polymer chains and thereby decrease the creep compliance of the copolymer. These two factors may be adjusted as necessary to produce an adhesive having the desired creep compliance.

Moisture Vapor Transmission Rate

Adhesives preferred for use as a pressure sensitive adhesive in wound dressings are those which permit passage of moisture vapor such as perspiration. Accordingly, the preferred materials are those with a twenty four hour moisture vapor transmission rate (MVTR $T_{24}$) of at least about 500 g/m$^2$, most preferably at least about 1000 g/m$^2$, when measured in accordance with ASTM E 96-80 at 40° C. with a humidity differential of 80%.

Skin Adhesion

The adhesive of this invention exhibits an initial skin adhesion ($T_0$) of between about 8 to 80 g/cm width, preferably between about 12 to 60 g/cm width; and a twenty four hour skin adhesion ($T_{24}$) of between about 8 to 160 g/cm width, preferably between about 12 to 80 g/cm width. Adhesives with an adhesion of less than about 8 g/cm width at any time during normal periods of use will result in premature peeling from the skin while adhesives with an adhesion of greater than about 160 g/cm width at the time of removal will produce significant skin irritation upon removal.

In addition, the adhesive exhibits a ($T_{WET}$) of at least about 8 g/cm width, preferably at least about 12 g/cm width.

Adhesive Lift

An adhesive which prematurely peels or delaminates from the skin is commercially unacceptable for use as a skin adhesive. Generally, an adhesive must exhibit an average adhesive lift rating (Lift) of less than about 2.5 to be useful as a skin adhesive.

The adhesive of this invention can be reproducibly synthesized with an acceptable adhesive Lift rating of less than about 2.5, typically below about 2, without interfering with the ability of the adhesive to meet the other characteristics required for consideration of the adhesive as an acceptable skin adhesive.

Adhesive Residue

An adhesive which leaves excessive residue behind is commercially unacceptable for use as a skin adhesive. Generally, an adhesive must exhibit an average adhesive residue rating (Residue) of less than about 2.5 to be useful as a skin adhesive.

The adhesive of this invention can be reproducibly synthesized with an acceptable Residue rating of less than about 2.5, typically below about 2, without interfering with the ability of the adhesive to meet the other characteristics required for consideration of the adhesive as an acceptable skin adhesive.

Skin Adhesion Profile

The "Skin Adhesion Profile" of an adhesive is a combination of the Skin Adhesion, Adhesive Lift and Adhesive Residue characteristics of the adhesive. A satisfactory "Skin Adhesion Profile" is a combination of Skin Adhesion, Adhesive Lift and Adhesive Residue which is subjectively acceptable to consumers. For example, an adhesive having superior skin adhesion but modest adhesive lift and adhesive residue may possess an unsatisfactory Skin Adhesion Profile while an adhesive having fair skin adhesion but superior adhesive lift and adhesive residue may possess a satisfactory Skin Adhesion Profile.

Immersion Absorption

The adhesive of the present invention possesses a twenty-four hour immersed absorption capacity (Imrs$_{24}$) of at least about 200%, preferably about 300% to 450%. This level of absorption capacity makes the adhesive well adapted for use in wound dressings intended to cover surgical incisions and lesions expected to exude moderate amounts of body fluids. For example, a ten centimeter square wound dressing having a 1 mil (0.025 cm) thick film of the adhesive of this invention rated at (Imrs$_{24}$) of 300% can be expected to absorb and retain about 7.5 ml of fluid in the adhesive.

Demand Absorption

The adhesive of the present invention possesses a demand absorption (Dmnd$_{15}$) (measured as the slope of the line through the point of the curve at 15 minutes and through the origin) of at least about 1.5 g/hr, preferably about 2.0 g/hr. This rate of absorption demand makes the adhesive well adapted for use in wound dressings intended to cover surgical incisions and lesions expected to exude moderate amounts of body fluids within a relatively short time span.

Polymerization Process

Monomers A, B, C and PX are free radical polymerized to form the precursor composition of this invention which may then be crosslinked to form the adhesive.

Solvent

The A, B, C and PX monomers may be dissolved in a suitable inert organic solvent for polymerization. The solvent must be effective for dissolving monomers A, B, C and PX as well as the resultant uncrosslinked copolymer. Suitable solvents include specifically, but not exclusively, single solvent systems, such as ethyl acetate; and cosolvent systems, such as mixtures of ethyl acetate/toluene and ethyl acetate/toluene/isopropyl alcohol. Other solvent systems are also believed to be useful.

The amount of solvent used must be sufficient to achieve intimate contact between the polymerization reactants including monomers A, B, C, and PX as well as the polymerization initiator and initiated polymer chains. Typically, use of about 30-80 wt % solvent, based on the total weight of reactants and solvent, is sufficient to achieve substantially complete polymerization within a reasonable time period.

In addition to the solvent-based technique, copolymerization of the monomers may be completed by other well known techniques such as suspension polymerization, emulsion polymerization, and bulk polymerization.

Polymerization Initiator

Polymerization of the solvent dissolved monomers is effected by standard free radical polymerization utilizing a suitable free radical initiator. Numerous free radical initiators are well known in the industry. Exemplary of those free radical initiators suitable for use in the present invention are those described in U.S. Pat. Re. No. 24,906 issued to Ulrich, the disclosure of which is herein incorporated by reference. Suitable thermally activated initiators include specifically, but not exclusively, azo compounds such as 2,2'-azo-bis(isobutyronitrile), tert-butyl hydroperoxide, benzoyl peroxide, and cyclohexanone peroxide. Generally, about 0.01 to 1 wt %, preferably about 0.01 to 0.5 wt %, initiator, based upon the total weight of all monomers in the copolymer, is effective for initiating polymerization.

Coating onto Substrate

The adhesive precursor may be coated onto a substrate to form various articles intended for adhesion to skin including tapes, patches, strips, wound dressings, monitoring or neuro-stimulating electrodes, drapes, etc. Without intending to be unduly limited thereby, the remainder of the discussion will be presented with respect to the manufacture of a wound dressing.

Wound Dressing Backings

Substrates suitable for use in the manufacture of a wound dressing intended for attachment to the skin include woven, nonwoven and knit fabrics and conformable synthetic films such as polypropylene, polyethylene, polyvinyl chloride, polyurethane, polyester, and ethyl cellulose.

Suitable woven and nonwoven fabrics include those formed from threads of synthetic or natural materials including cotton, nylon, rayon, polyester, and the like. Synthetic films suitable for use are those having a tensile modulus of less than about 400,000 psi (2758.8 MPa), preferably less than about 300,000 psi (2069.1 MPa), measured in accordance with ASTM D-638.

The fabric should be sufficiently continuous to prevent the passage of pathogens such as bacteria from entering the wound.

The preferred substrates are those which permit visual inspection of the wound without removal of the dressing and permit passage of body fluids such as perspiration and wound exudate. Accordingly, preferred materials are those which are transparent and possess a twenty four hour moisture vapor transmission rate (MVTR $T_{24}$) of at least about 500 g/m$^2$, most preferably at least about 1000 g/m$^2$ when measured in accordance with ASTM E 96-80 at 40° C. with a humidity differential of 80%.

A continuous polyurethane film sold by B. F. Goodrich under the trademark "Estane TM" and a continuous polyester film sold by E. I. Dupont DeNemours sold under the trademark "Hytrel TM" each have an MVTR $T_{24}$ value of about 1000 to 1500 g/m$^2$. Woven substrates, such as that sold by Minnesota Mining and Manufacturing Company and used in "Durapore TM" surgical tape possess even higher MVTR $T_{24}$ values.

Coating Techniques

The copolymer precursor can be coated onto the substrate by any of a variety of conventional techniques such as roll coating, spray coating, extrusion coating, coextrusion, hot-melt coating and the like. The process of choice depends upon the nature of the substrate employed. For example, a preferred method for coating the adhesive upon a nonwoven fabric is to dissolve the adhesive copolymer in an organic solvent, spread the copolymer solvent onto a release liner, and then laminate the adhesive coating onto the nonwoven fabric before the adhesive is completely dry.

As mentioned previously, use of the preferred photosensitive crosslinking agent in the copolymer of this invention allows the use of solventless coating techniques because the copolymer need not be crosslinked until after it is coated upon a support member. For example, the adhesive may be coated without the aid of a solvent by (i) stripping solvent remaining from polymerization by any of the well known conventional techniques, (ii) coating the dried, uncrosslinked polymer onto a suitable substrate by any of the well known conventional "hot melt" techniques such as an extrusion or rotogravure process, and then (iii) crosslinking the coated polymer to form an absorbent pressure sensitive adhesive film.

Crosslinking

The coated adhesive precursor is then crosslinked by contacting or exposing the precursor to the appropriate crosslinking initiator such as ultraviolet radiation at an intensity and for a duration sufficient to crosslink the copolymer by means of the PX monomer.

The extent to which the copolymer is crosslinked depends upon both the amount of PX monomer in the copolymer and the intensity of the treatment. For purposes of quality control, the degree to which the copolymer is crosslinked is preferably controlled by treating the copolymer so as to effect substantially complete crosslinking of the PX monomer and adjusting the amount of PX monomer as necessary.

When a photosensitive PX monomer is employed, ultraviolet radiation treatment is conveniently effected using medium-pressure mercury lamps providing an output of about 80 watts per cm (200 watts per inch) and having a spectral output over a range of about 180 to 430 nanometers.

Sterilization

When the adhesive is intended for use in a wound dressing, the adhesive must be sterilized. A widely accepted method of sterilizing wound dressings is to subject the dressing to about 2.5 to 5 megarads of gamma radiation.

Testing Protocols

Inherent Viscosity (IV) (Degree of Polymerization)

The inherent viscosity of a polymer is measured in accordance with the protocol described by Fred W. Billmeyer, Jr. at pages 84–85 of the textbook entitled *Textbook of Polymer Science*, Second Edition, published by Wiley-Interscience, (1971). Briefly, solution viscosity is measured by comparing the efflux time (t) required for a specified volume of polymer solution to flow through a capillary tube with the corresponding efflux time ($t_0$) for the solvent. The measured variables t, $t_0$, and solute concentration (c) are then used to calculate inherent viscosity (also known as Logarithmic Viscosity) using the equation:

$$\eta = (\ln t/t_0)/c$$

Creep Compliance

The adhesive to be tested is knife-coated onto a smooth film of polytetrafluoroethylene to a thickness of 150 micrometers. The adhesive coating is dried to constant weight in an air-circulating oven (at least five minutes at 110° C.). The dried adhesive is stripped from the polytetrafluoroethylene support to form a dried adhesive film.

Two identical test specimens are die-cut from the dried adhesive film and positioned on a Parallel Plate Creep Compliance Rheometer. One of the specimens is laminated to each side of a rigid metal center plate and then sandwiched between rigid metal outer plates to form a plate/adhesive/plate/adhesive/plate laminate. Screws connecting the outer plates are tightened to compress the interposed test specimens approximately 10%.

The specimen-containing plates are positioned horizontally within the rheometer with one end of the center plate electronically connected to a chart recorder and the other end attached to a flexible wire. The flexible wire is extended horizontally from the center plate, directed downward around a pulley, and connected to a 500 gram weight. The outer plates are held in a fixed position.

The size of the weight is selected to measurably deform the test specimen a distance no greater than its thickness.

A strip chart recorder is started and the variables of time (t), displacement (Strain) and applied force (Stress) are recorded. The creep compliance of the tested adhesive is then calculable in cm²/dyne using the equation:

$$J_{(t)} = (2AX)/(hf)$$

where:
(t) is the time at which the measurement is taken (hrs),
(A) is the area of one major surface of the adhesive sample (cm²),
(h) is the thickness of the adhesive sample after compression (cm),
(X) is the displacement at time t (where X is less than h) (cm), and
(f) is the force exerted on the center plate by the weight attached to the end of the flexible wire (dynes).

Moisture Vapor Transmission Rate (Upright)

The Moisture Vapor Transmission Rate ($MVTR_{Up}$) is measured in accordance with ASTM E 96-80 as modified below.

Thirty five millimeter diameter samples of a 0.025 cm thick film of the adhesive is laminated to a 0.0275 cm thick polyurethane web having a $MVTR_{up}$ $T_{24}$ of 2,000 to 2,400 g/m² measured at 40° C. and a relative humidity differential of 80%.

The laminated samples are sandwiched between the adhesive surfaces of two axially aligned foil adhesive rings having 2.54 cm diameter holes. Each sample is pulled to ensure a flat, wrinkle-free and void-free foil/sample/foil laminate.

A four-ounce (0.14 kg) glass jar is filled half-full with distilled water. The jar is fitted with a screw-on cap having a 3.8 cm diameter hole concentrically aligned with a rubber washer having a 4.445 cm outside-diameter and a 2.84 cm inside-diameter.

The foil/sample/foil laminate is concentrically positioned on the rubber washer and the sample-containing sub-assembly screwed loosely onto the jar.

The assembly is placed into a chamber maintained at a temperature of 40° C. and 20% relative humidity. The assembly is removed from the chamber after four hours, weighed to the nearest 0.01 gram ($W_1$), and immediately returned to the chamber. The cap is now screwed tightly onto the jar without bulging of the sample. The assembly is again removed from the chamber after an additional eighteen hours and weighed to the nearest 0.01 gram ($W_2$).

The $MVTR_{up}$ $T_{24}$ of the adhesive (measured in grams of water transmitted per square meter of sample area over a twenty four hour period) may then be calculated according the formula set forth below:

$$MVTR_{up}\ T_{24} = (W_1 - W_2)(4.74 \cdot 10^4)/t$$

where:
($W_1$) is the initial weight of the assembly (grams)
($W_2$) is the final weight of the assembly (grams), and
(t) is the time period between $W_1$ and $W_2$ (hrs).

Three samples of each adhesive were run and the average of the three samples reported.

Moisture Vapor Transmission Rate (Inverted)

The protocol for measuring $MVTR_{invt}$ is the same as the "Upright" protocol except that the assembly is inverted inside the chamber once the cap is tightly screwed onto the jar so that the water within the jar directly contacts the foil/sample/foil laminate while the assembly is within the chamber.

Skin Adhesion

Evaluation of the adhesiveness of a composition to human skin is an inherently temperamental determination. Human skin possesses wide variations in composition, topography, and the presence/absence of various body fluids. However, controlled and comparative values of adhesion are attainable by employing a select panel of individuals trained to recognize the normal skin variations encountered in medical practice.

Initial skin adhesion ($T_0$), skin adhesion after 24 hours of continuous contact with the skin ($T_{24}$), and skin adhesion to wet skin ($T_{WET}$) is measured in accordance with the widely accepted PSTC-1 Peel Adhesion Test for single coated adhesive tape conducted at a removal angle of 180°. The PSTC-1 Peel Adhesion Test is a testing protocol established by the Specifications and Technical Committee of the Pressure Sensitive Tape Council located at 5700 Old Orchard Road, Skokie, Ill. The test is modified for our purposes by applying the tape to the skin of a living human.

The adhesive is tested as a 0.025 cm film coated onto a 0.0275 cm thick polyurethane web having a $MVTR_{up}$ $T_{24}$ of 2,000 to 2,400 g/m$^2$ measured at 40° C. and a relative humidity differential of 80%. Three samples measuring 2.5 cm wide by 7.6 cm long are applied to the back of each of six human subjects (three men and three women). The subjects are placed in a prone positioned with arms at their sides and heads turned to one side. Samples are applied to both sides of the spinal column with the length of each sample positioned at a right angle to the spinal column. The samples are applied without tension or pulling of the skin.

Those samples tested for wet skin adhesion are applied to skin which had been moistened with a water saturated cloth, leaving visually observable drops of standing water, immediately before application of the sample.

The samples are pressed into place with a 2 kg roller moved at a rate of approximately 2.5 cm/sec with a single forward and reverse pass. No manual pressure should be applied to the roller during application.

The samples are then removed either immediately after application ($T_0$) or after 24 hours of continuous contact with the skin ($T_{24}$), at a removal angle of 180° and removal rate of 15 cm per minute, using a conventional adhesion tester equipped with 25 lb (11.4 kg) test line attached to a 2.5 cm clip. The clip is attached to the edge of the sample furthest from the spinal column by manually lifting about 1 cm of the sample from the skin and attaching the clip to the raised edge. The adhesion tester is a strain-gauge mounted on a motor-driven carriage.

The measured force required to effect removal is reported in grams per cm.

Adhesive Lift

Evaluation of the adhesive tenacity of a composition to human skin is an inherently temperamental determination for the same reasons established above in connection with evaluation of the adhesiveness of a composition to human skin.

However, the observational values as to adhesive tenacity (Lift) are generally reproducible and in accord with subjective assessments of similar properties which are widely accepted in the art as meaningful, reliable and reproducible.

The Adhesive Lift Test is a subjective assessment of the extent to which adhesive tape prematurely separates from the body after application of a sample in accordance with the Skin Adhesion Test. The applied samples are visually inspected just prior to testing for Skin Adhesion (i.e. twenty four hours after application) to determine the extent to which the edges of the sample have separated from the skin. Each sample is assigned a numerical rating from 0 to 5 based on the following observation:

| Rating | Definition |
| --- | --- |
| 0 | No visible separation. |
| 1 | Separation at edges of tape only. |
| 2 | Separation of 1% to 25% of tape area. |
| 3 | Separation of 26% to 50% of tape area. |
| 4 | Separation of 51% to 75% of tape area. |
| 5 | Separation of 76% to 100% of tape area. |

Each sample is assigned a single whole number from the list established above by each panel member. The assigned values from the panel members are then averaged and reported to the tenths position. Due to the subjective nature of the test, differences of less than 0.5 in averaged residue values should be considered substantially the same.

Adhesive Residue

As with the rating of Adhesive Lift, an assessment of the Adhesive Residue Rating (Residue) of a composition to human skin is an inherently temperamental but reproducible determination.

The Adhesive Residue Test is a subjective assessment of the amount of adhesive left upon the skin after removal of an adhesive sample in accordance with the Skin Adhesion Test. The skin directly underlying each sample was visually inspected to determine the extent to which the area contacted by the adhesive contains residual adhesive. Each sample was then assigned a numerical rating from 0 to 5 based on the following observation:

| Rating | Definition |
| --- | --- |
| 0 | No visible residue. |
| 1 | Residue at edges of tape only. |
| 2 | Residue covering 1% to 25% of tested area. |
| 3 | Residue covering 26% to 50% of tested area. |
| 4 | Residue covering 51% to 75% of tested area. |
| 5 | Residue covering 76% to 100% of tested area. |

Each sample was assigned a single whole number from the list established above by each panel member. The assigned values from the panel members were then averaged and reported to the tenth position. Due to the subjective nature of the test, differences of less than 0.5 in averaged residue values should be considered substantially the same.

Preferred skin adhesives will generally exhibit an average residue rating below about 2.5.

Absorption (Immersion)

The Water absorptive capacity of an adhesive is measured by immersing the adhesive into buffered water and measuring the weight of water absorbed.

Round test samples having a 5 cm$^2$ surface area are preweighed ($W_i$) and placed into a 180 ml bottle containing 30 ml of phosphate buffered saline solution having a pH of 7.2 purchased from Sigma Chemical Company. The bottles are capped and allowed to stand without agitation. The samples are removed 24 hours after initial immersion in the bottle and weighed ($W_f$). The Absorbency Value is calculable using the following formula:

$$Imrs_{24} = [(W_f - W_i)/W_i] \times 100$$

Absorption (Demand)

The initial rate at which an adhesive is able to absorb water is measured by contacting a sample of the adhesive with buffered water, periodically measuring the weight of water absorbed, plotting the weight of water absorbed verses time, and measuring the slope of a line through the origin of the plot and the data point at 15 minutes.

Equipment

Feeding Plate

A water feeding plate is constructed from (i) a ⅜ inch thick six inch diameter plexiglass base plate, (ii) a ½ inch thick six inch diameter plexiglass top plate, (iii) a sixty mm diameter Corning 60C TM fritted glass disc, (iv) two, two-way valves, and (v) one 3½ inch and one 4 inch diameter O-ring.

The base plate is machined to provide (a) a ½ inch deep, three inch diameter, central cylindrical reservoir, (ii) a pair of radially opposed passages extending completely through the sides of the plate into communication with the reservoir, and (c) concentric 3½ inch diameter and 4 inch diameter grooves. The two-way valves are sealing fitted into the bores and the O-rings positioned within the grooves.

The top plate is machined to provide a sixty mm central hole into which the glass frit is sealed with silicone adhesive. The top surface of the glass frit is positioned flush with the top surface of the plate.

The top plate is secured over the base plate using four machine screws spaced along the periphery of the plates which pass through orifices drilled in the top plate and extend into axially aligned bores within the bottom plate.

Supply Tank

A 19 cm diameter supply tank of phosphate buffered saline solution is connected with rubber tubing to a first of the valves attached to the Feeding Plate. The tank is covered to prevent evaporation of the saline solution but is NOT sealed. The tank is placed upon a standard Lab Jack so that the vertical position of the tank may be raised and lowered as necessary to generate zero head pressure at the surface of the glass frit in the feeding plate.

Balance

The feeding plate is placed upon the pan of a standard electronic balance to permit changes in the weight of the feeding plate to be measured and recorded.

Procedure

The reservoir is filled with saline solution from the supply tank and bubbles removed by opening the second of the two-way valves connected to the feeding plate. The tank is then vertically positioned to provide zero head pressure within the reservoir.

A six centimeter diameter disc of Whatmann No. 1 filter paper is positioned on the glass frit to prevent the adhesive from bonding to the frit.

An oversized sample of the adhesive to be tested (one which more than covers the glass frit) is centered over the glass frit. The balance is tared to zero and the cumulative weight of saline solution absorbed by the adhesive sample weighed over time.

The height of the supply tank is NOT readjusted during the experiment unless more than 20 grams of saline solution is removed from the tank due to absorption or evaporation. Should more than twenty grams of saline be removed from the tank the vertical height of the tank is repositioned once immediately after the twenty grams have been removed to compensate for the decrease in head pressure generated by the saline solution within the tank.

The increased weight is plotted against time and a "Demand Absorption Value" ($Dmnd_{15}$) determined by measuring the slope of a line through the origin of the plot and the curve at fifteen minutes.

The invention will be further illustrated by reference to the following non-limiting Examples. All parts and percentages are expressed as parts by weight unless otherwise indicated.

Examples 1-51

Into a 0.95 liter amber bottle was placed the respective amounts of (i) isooctyl acrylate (Monomer A) prepared by Fischer esterification of acrylic acid with Exxal-8 obtained from Exxon Corporation (except for Examples 14-16, where butyl acrylate (BA), available from Union Carbide, was employed), (ii) N-vinyl pyrrolidone (Monomer B) obtained from General Aniline & Film Corporation, (iii) a 46 solids wt % toluene solution of polyethylene oxide acrylate (n=16, except for Examples 17-51 where n=9) (Monomer C) prepared by Fischer esterification of Carbowax TM 750 with acrylic acid (calculated upon dry monomer) for n=16, or purchased as 100% solids from Shin Nakamura for n=9, (iv) a 26 wt % ethyl acetate solution of acryloxybenzophenone (Monomer PX) (calculated upon dry monomer), (v) an analytical reagent grade ethyl acetate, and (vi) an analytical reagent grade isopropyl alcohol. The specific amount of each of these components (in grams) used to form the pressure sensitive adhesives of Examples 1-51 is given in TABLE 1.

For each of the Example compositions, the solution was deoxygenated by purging the bottle with nitrogen at a rate of one liter per minute for three minutes. The deoxygenated bottle was sealed and placed in a rotating water bath maintained at 55° C. for twenty four hours to effect substantially complete polymerization of monomers A, B, C and PX.

The Inherent Viscosity (IV), Creep Compliance ($J_3$), the twenty four hour Moisture Vapor Transmission Rate (Upright) ($MVTR_{up}$ $T_{24}$), the twenty four hour Moisture Vapor Transmission Rate (Inverted) ($MVTR_{Invt}$ $T_{24}$), Skin Adhesion (Initial) ($T_0$), Skin Adhesion (Twenty Four Hours) ($T_{24}$), Skin Adhesion (Wet) ($T_{WET}$), Adhesive Lift (Lift), Adhesive Residue (Res), Absorption (Immersion) ($Imrs_{24}$), and Absorption (Demand) ($Dmnd_{15}$) of the samples were then measured in accordance with the testing protocols set forth herein. The results of such testing are set forth in TABLE 2 below. The extent to which the polymers were crosslinked by exposure to ultraviolet radiation prior to testing is also set forth in TABLE 2.

TABLE 1

Amount of each component in grams used to from the pressure sensitive adhesives of Examples 1-51.

| Ex. Nos. | IOA | NVP | EOA | ABP | EtOAc | IPA |
|---|---|---|---|---|---|---|
| 1-3 | 75.0 | 100.0 | 75.0 | 0.96 | 129.5 | 35.0 |
| 4-7 | 133.1 | 79.2 | 81.5 | 0.96 | 180.9 | 25.0 |

TABLE 1-continued

Amount of each component in grams used to from the pressure sensitive adhesives of Examples 1-51.

| Ex. Nos. | IOA | NVP | EOA | ABP | EtOAc | IPA |
|---|---|---|---|---|---|---|
| 8-10 | 174.8 | 37.5 | 81.5 | 0.96 | 188.5 | 17.5 |
| 11-13 | 143.5 | 37.5 | 149.5 | 0.96 | 146.8 | 22.5 |
| 14-16 | 109.9 | 69.9 | 152.1 | 0.96 | 92.6 | 40.0 |
| 17-23 | 79.9 | 40.4 | 80.0 | 0.2 | 167.8 | 32.3 |
| 24-30 | 94.8 | 40.0 | 65.0 | 0.2 | 171.4 | 28.6 |
| 31-39 | 79.8 | 70.0 | 50.0 | 0.2 | 161.4 | 38.6 |
| 40-46 | 81.8 | 54.0 | 64.0 | 0.2 | 163.6 | 36.4 |
| 47-51 | 79.8 | 70.0 | 39.7 | 0.2 | 153.9 | 37.8 |

IOA = Isooctyl acrylate
NVP = N-vinylpyrrolidone
EOA = Ethylene oxide acrylate
ABP = 4-acryloxybenzophenone
EtOAc = ethyl acetate
IPA = isopropyl alcohol

TABLE 2

| Ex. No. | Ratio (IOA/NVP/EOA$^9$/ABP) | IV | UVmj | MRad | $J_3$ | MVTR up | MVTR invt | $T_0$ | $T_{24}$ | Lift | Res | $T_{WET}$ | Imrs$_{24}$ | Dmnd$_{15}$ |
|---|---|---|---|---|---|---|---|---|---|---|---|---|---|---|
| 1 | 30/40/29.9@/0.1 | 0.84 | 100 | | 0.41 | | | | | | | | | |
| 2 | | | 200 | | 0.44 | 2148 | 2997 | 33 | 160 | 2.0 | 0.9 | 26 | 177 | 2.0 |
| 3 | | | 300 | | 0.43 | | | | | | | | | |
| 4 | 53.2/31.7/15@/0.1 | 0.91 | 100 | | 1.42 | | | 135 | 510 | 0.9 | 1.7 | | | |
| 5 | | | 200 | | 1.39 | 1180 | 1060 | 76 | 407 | 1.4 | 1.3 | 30 | 65 | 0.4 |
| 6 | | | 200 | | | | | 67 | 474 | 1.1 | 1.6 | | | |
| 7 | | | 300 | | 1.36 | | | 53 | 317 | 1.2 | 0.9 | | | |
| 8 | 69.9/15/15@/0.1 | 0.87 | 100 | | X | | | | | | | | | |
| 9 | | | 200 | | X | 1250 | 1412 | 124 | 118 | 1.7 | 3.7 | 39 | 32 | |
| 10 | | | 300 | | 8.12 | | | | | | | | | |
| 11 | 57.4/15/27.5@/0.1 | 0.96 | 100 | | X | | | | | | | | | |
| 12 | | | 200 | | X | 1792 | 6504 | 87 | 67 | 1.7 | 4.1 | 41 | 145 | 1.6 |
| 13 | | | 300 | | 8.96 | | | | | | | | | |
| 14 | 43.9#/28/28@/0.1 | 1.05 | 100 | | 6.27 | | | | | | | | | |
| 15 | | | 200 | | 6.28 | 1998 | 8322 | 54 | 89 | 2.6 | 0.0 | 26 | 47 | 2.3 |
| 16 | | | 300 | | 5.01 | | | | | | | | | |
| 17 | 39.9/20/40/0.1 | 0.76 | 0 | 0 | No Test | | | | | | | | | |
| 18 | | | 0 | 2.71 | | 1936 | 9493 | 134 | 160 | 1.8 | 2.5 | 21 | | |
| 19 | | | 0 | 3.16 | | | | 155 | 193 | 1.8 | 0.7 | | | |
| 20 | | | 100 | | | | | 123 | 156 | 2.8 | 1.0 | 54 | | |
| 21 | | | 200 | 0 | 6.43 | 2002 | 6952 | 31 | 24 | 3.2 | 0.0 | 15 | | |
| 22 | | | 200 | 2.94 | 5.51 | | | 15 | 0 | 5.0 | | | 360 | 2.6 |
| 23 | | | 300 | | | | | | | | | | | |
| 24 | 47.4/20/32.5/0.1 | 0.81 | 0 | 0 | No Test | | | | | | | | | |
| 25 | | | 0 | 2.71 | | 1738 | 7953 | 135 | 240 | 1.3 | 2.7 | 22 | | |
| 26 | | | 0 | 3.16 | | | | 164 | 268 | 1.0 | 0.7 | | | |
| 27 | | | 100 | | | | | 108 | 232 | 1.5 | 0.5 | 31 | | |
| 28 | | | 200 | 0 | 3.08 | 1724 | 5458 | 33 | 72 | 1.7 | 0.0 | 14 | | |
| 29 | | | 200 | 2.94 | 1.40 | | | 24 | 44 | 2.2 | 0.0 | | 304 | 1.6 |
| 30 | | | 300 | | | | | | | | | | | |
| 31 | 39.9/35/25/0.1 | 0.88 | 0 | 0 | 5.51 | | | | | | | | | |
| 32 | | | 0 | 2.71 | | 1909 | 9052 | 37 | 161 | 2.0 | 0.8 | 24 | | |
| 33 | | | 0 | 3.16 | | | | 83 | 209 | 1.7 | 0.0 | | | |
| 34 | | | 50 | 3.21 | 1.12 | | | | | | | | | |
| 35 | | | 50 | | 2.39 | | | 25 | 104 | 2.1 | 0.1 | | | |
| 36 | | | 100 | | 1.87 | | | 31 | 124 | 3.3 | 0.0 | 19 | | |
| 37 | | | 200 | 2.94 | 0.70 | | | 10 | 13 | 4.2 | 0.0 | | 655 | 2.4 |
| 38 | | | 200 | 0 | 1.16 | 1882 | 5622 | 16 | 39 | 2.3 | 0.0 | 15 | | |
| 39 | | | 300 | | | | | | | | | | | |
| 40 | 40.9/27/32/0.1 | 0.79 | 0 | 0 | 10.23 | | | | | | | | | |
| 41 | | | 0 | 3.16 | | | | 142 | 225 | 1.8 | 0.3 | | | |
| 42 | | | 0 | 2.71 | | 1962 | 8835 | 85 | 202 | 2.0 | 2.0 | 34 | | |
| 43 | | | 100 | | | | | 88 | 173 | 2.8 | 0.0 | 34 | | |
| 44 | | | 200 | 0 | 2.02 | 1882 | 5918 | 25 | 40 | 3.3 | 0.0 | 14 | | |
| 45 | | | 200 | 2.94 | 1.02 | | | 13 | 7 | 4.5 | 0.0 | | 437 | 2.2 |
| 46 | | | 300 | | | | | | | | | | | |
| 47 | | | 50 | | | | | 109 | 173 | 1.3 | 0.2 | | | |
| 48 | 42/36.8/20.90/0.3 | 0.74 | 57 | | 2.68 | | | | | | | | 674 | |
| 49 | | | 108 | | 2.18 | | | | | | | | | |
| 50 | | | 200 | | | | | 54 | 150 | 1.8 | 0.2 | | | |
| 51 | | | 208 | | | | | 11 | 68 | 1.9 | 0.2 | | 442 | |

LEGEND

| Symbol | Meaning (units) |
|---|---|
| Imrs$_{24}$ | Absorption measured by the Immersion Technique (% of sample weight) |
| Dmnd$_{15}$ | Absorption measured by the Demand Technique expressed as the slope of the line through the origin and at a point 15 minutes on the demand curve (g/hr) |
| IV | Inherent Viscosity (dl/g) |
| $J_3$ | Creep Compliance Measured After Three Minutes (cm$^2$/dyne · 10$^{-5}$) |

TABLE 2-continued

| | |
|---|---|
| Lift | Lift (Extent of Premature Peeling) |
| MRad | Sterilizing Gamma Radiation (megarads) |
| Res | Adhesive Residue (Extent to which residual adhesive remains on skin) |
| UVmj | Ultra Violet Radiation (millijoules/cm$^2$) |
| MVTR$_{Up}$ | Moisture Vapor Transmission Rate Measured with Upright Cup (g/m$^2$ for 24 hrs) |
| MVTR$_{Invt}$ | Moisture Vapor Transmission Rate Measured w/ an Inverted Cup (g/m$^2$ for 24 hrs) |
| T$_0$ | Skin Adhesion at time (t) = 0 hrs (grams/2.54 cm width) |
| T$_{24}$ | Skin Adhesion at time (t) = 24 hrs (grams/2.54 cm width) |
| T$_{WET}$ | Skin Adhesion to Wet Skin at time (t) = 0 hrs (grams/2.54 cm width) |

IOA = Isooctyl acrylate
NVP = N-vinylpyrrolidone
EOA$^9$ = Ethylene oxide acrylate with an average of 9 EO units per molecule.
EOA$^{16}$ = Ethylene oxide acrylate with an average of 16 EO units per molecule.
ABP = 4-acryloxybenzophenone
@ = EOA$^{16}$
BA = butyl acrylate While in accordance with the patent statutes, description of the preferred weight fractions, and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A wound dressing comprising a substrate coated with an absorbent pressure-sensitive adhesive on a major surface thereof, and a release liner protectively sandwiching the adhesive between the substrate and the liner; the pressure-sensitive adhesive having a twenty-four hour immersed absorption capacity (Imrs$_{24}$) of at least 200 percent and comprising a crosslinked copolymer of A, B, C, and PX wherein:
   (a) A is a monomer selected from the group consisting of (i) an acrylate or methacrylate ester of a non-tertiary C$_{4-12}$ alcohol, and (ii) an acrylate or methacrylate ester of a mixture of non-tertiary C$_{1-4}$ alcohols averaging between about 4–12 carbon atoms per alcohol molecule;
   (b) B is a hydrophilic alkylene oxide acrylate monomer having an average of about 3 to 40 alkylene oxide units;
   (c) C is a hydrophilic N-vinyl lactam monomer; and
   (d) PX is a crosslinking monomer effective for crosslinking the copolymer.

2. The wound dressing of claim 1 wherein: (a) monomer B of the pressure-sensitive adhesive is an ethylene oxide acrylate having an average of about 5 to 20 ethylene oxide units, (b) monomer C of the pressure-sensitive adhesive is N-vinyl pyrrolidone, N-vinyl-2-caprolactam, or combinations thereof, and (c) crosslinking monomer PX of the pressure-sensitive adhesive is 4-acryloxybenzophenone.

3. The wound dressing of claim 1 wherein the adhesive comprises about 30 to 70 wt % monomer A, about 15 to 40 wt % monomer B, about 15 to 50 wt % monomer C, and about 0.01 to 2 wt % crosslinking monomer PX.

4. The wound dressing of claim 1 wherein the pressure sensitive adhesive has a twenty-four hour moisture vapor transmission rate (MVTR$_{up}$ T$_{24}$) of at least about 500 g/m$^2$.

5. The wound dressing of claim 1 wherein the pressure sensitive adhesive has a demand absorption value (Dmnd$_{15}$) of at least 1.5 g/hr.

* * * * *